United States Patent
Orecchia et al.

(10) Patent No.: US 6,929,157 B2
(45) Date of Patent: Aug. 16, 2005

(54) MULTIPLE USE DENTAL VISCOUS MATERIAL DISPENSER

(75) Inventors: Mike Orecchia, Westminster, CO (US); Rick Taylor, Lafayette, CO (US)

(73) Assignee: Confi-Dental Products Co., Louisville, CO (US)

( * ) Notice: Subject to any disclaimer, the term of this patent is extended or adjusted under 35 U.S.C. 154(b) by 0 days.

(21) Appl. No.: 10/373,179

(22) Filed: Feb. 26, 2003

(65) Prior Publication Data

US 2004/0164097 A1 Aug. 26, 2004

(51) Int. Cl.⁷ ................................................ B67D 5/42
(52) U.S. Cl. ...................................... 222/326; 222/391
(58) Field of Search ................................ 222/326, 327, 222/386, 391, 1; 433/90

(56) References Cited

U.S. PATENT DOCUMENTS

| | | | |
|---|---|---|---|
| 2,648,906 A | 8/1953 | Holmes | |
| 2,837,824 A | 6/1958 | Moller | |
| 3,581,399 A | 6/1971 | Dragan | |
| 4,198,756 A | 4/1980 | Dragan | |
| 4,295,828 A | 10/1981 | Rudler | |
| 4,330,280 A | 5/1982 | Dougherty et al. | |
| 4,384,853 A | 5/1983 | Welsh | |
| 4,472,141 A | 9/1984 | Dragan | |
| 4,802,607 A * | 2/1989 | Johnson | 222/82 |
| 4,813,871 A | 3/1989 | Friedman | |
| D315,956 S | 4/1991 | Dragan | |
| 5,061,179 A | 10/1991 | Dragan | |
| 5,125,836 A | 6/1992 | Dragan et al. | |
| 5,165,890 A | 11/1992 | Discko, Jr. | |
| 5,172,807 A | 12/1992 | Dragan et al. | |
| D334,803 S | 4/1993 | Discko, Jr. | |
| 5,267,859 A | 12/1993 | Discko, Jr. | |
| 5,306,147 A | 4/1994 | Dragan et al. | |
| 5,336,088 A | 8/1994 | Discko, Jr. | |
| D353,673 S | 12/1994 | Discko, Jr. et al. | |
| D357,536 S | 4/1995 | Dragan et al. | |
| D359,119 S | 6/1995 | Dragan et al. | |
| D359,560 S | 6/1995 | Mitchell | |
| 5,489,207 A | 2/1996 | Dragan et al. | |
| 5,707,234 A | 1/1998 | Bender | |
| 5,743,431 A * | 4/1998 | Brattesani | 222/1 |
| 5,743,436 A * | 4/1998 | Wilcox et al. | 222/137 |
| 5,871,355 A | 2/1999 | Dragan et al. | |
| 6,045,005 A * | 4/2000 | Stratton | 222/83.5 |
| 6,047,861 A * | 4/2000 | Vidal et al. | 222/137 |
| 6,059,570 A | 5/2000 | Dragan et al. | |
| 6,099,307 A | 8/2000 | Discko, Jr. | |
| 6,116,414 A | 9/2000 | Discko, Jr. | |
| 6,135,771 A | 10/2000 | Dragan et al. | |
| D435,292 S | 12/2000 | Dragan et al. | |
| 6,170,714 B1 * | 1/2001 | Lesage | 222/326 |
| 6,379,152 B1 | 4/2002 | Dragan | |
| D460,822 S | 7/2002 | Dragan et al. | |
| 6,422,866 B2 | 7/2002 | Dragan et al. | |
| D461,247 S | 8/2002 | Dragan et al. | |
| 6,585,696 B2 * | 7/2003 | Petersen et al. | 604/191 |

* cited by examiner

*Primary Examiner*—Joseph A. Kaufman
(74) *Attorney, Agent, or Firm*—Arent Fox, PLLC

(57) ABSTRACT

A viscous material dispenser, and dispenser system and kit, can include a dispenser without a dispensing tip and one or a plurality of separate dispensing tips that are removably attachable to the dispenser. The dispenser can be used with many different types of viscous material containing capsules and cartridges, such as those containing composites, dental cements, glass ionomers and the like. In embodiments, the dispenser can incorporate an integral activator for multi-component composition cartridges, such as glass ionomer cartridges.

15 Claims, 2 Drawing Sheets

MULTIPLE USE DENTAL VISCOUS MATERIAL DISPENSER

BACKGROUND OF THE INVENTION

1. Field of the Invention

This invention relates to a viscous material dispenser, and particularly to a multiple use dental syringe having exchangeable tips and/or an integral activator for activating multicomponent capsules.

2. Description of the Related Art

Various dispensing devices for dispensing viscous dental compositions are known in the art, such as, for example, those disclosed in U.S. Pats. Nos. 6,422,866; 6,379,152; 6,135,771; 6,116,414; 6,099,307; 6,059,570; 5,871,355; 5,707,234; 5,489,207; 5,336,088; 5,306,147; 5,267,859; 5,172,807; 5,165,890; 5,125,836; 5,061,179; 4,813,871; 4,619,613; 4,492,576; 4,472,141; 4,384,853; 4,330,280; 4,315,743; 4,295,828; 4,198,756; 4,084,320; 3,828,434; 3,760,503; 3,618,216; 3,581,399; 3,436,828; 3,346,147; 2,903,794; 2,837,824; 2,648,906; 683,075; Des. 461,247; Des. 460,822; Des. 435,292; Des. 359,560; Des. 357,141; Des. 359,119; Des. 357,536; Des. 353,673; Des. 334,803; and Des. 315,956; the subject matter of all of which are hereby incorporated by reference in their entireties.

U.S. Pat. No. 4,472,141 to Dragan discloses an attempt to achieve an all purpose dental syringe and delivery system for dispensing various types of dental materials. The Dragan syringe includes a power handle having a plunger that is incrementally advanced upon each actuation of the power handle and a plurality of interchangeable barrel assemblies, each with an associated dispensing nozzle. Dragan also discloses interchangeable plunger tips co-operatively associated with the plunger for complementing a particular barrel assembly.

However, providing interchangeable barrel assemblies including tips increases the costs incurred in a syringe device. Additionally, requiring the end user to remove a barrel, remove an associated plunger tip, replace the plunger tip with a different plunger tip, and then install a different barrel can be a time consuming procedure for the end user of the syringe device.

Additionally, certain viscous dental composition cartridges contain two or more separated components that must be mixed before application of the composition to a patient. Generally, a device that is separate from the dental syringe is used to break a frangible seal or the like separating the components. For example, in one conventional device, the cartridge is inserted into a slot and a device is used to apply pressure against the walls of the cartridge, breaking the seal separating the components and thus activating the viscous composition.

SUMMARY OF THE INVENTION

It is an object of this invention to overcome the deficiencies and limitations of the known viscous dispensing syringes.

It is another object of this invention to provide a viscous material dispenser which has interchangeable tips for holding various types of viscous material containing capsules, cartridges and/or the like.

It is still another object of this invention to provide an integral mechanism for activating multi-component viscous material containing cartridges.

These and other objects of this invention are achieved by a viscous material dispenser that has different tips that can be attached to the end of a barrel of the dispenser so that different types of composites, dental cements, and the like, as well as with glass ionomer type compositions, can be dispensed. The viscous material dispenser can also be constructed such that multi-component cartridges, for example containing activatable glass ionomer compositions, can be activated without the need for a separated activating tool. The viscous material dispenser can include a ratchet mechanism that enables dispensing of an intended amount of viscous material and also assist in locking a composite tip or capsule in position.

BRIEF DESCRIPTION OF THE DRAWINGS

The above and other objects, features and advantages of this invention will become apparent from the following description of preferred embodiments taken in conjunction with the accompanying drawings, in which.

DESCRIPTION OF THE PREFERRED EMBODIMENTS

Figure 1:
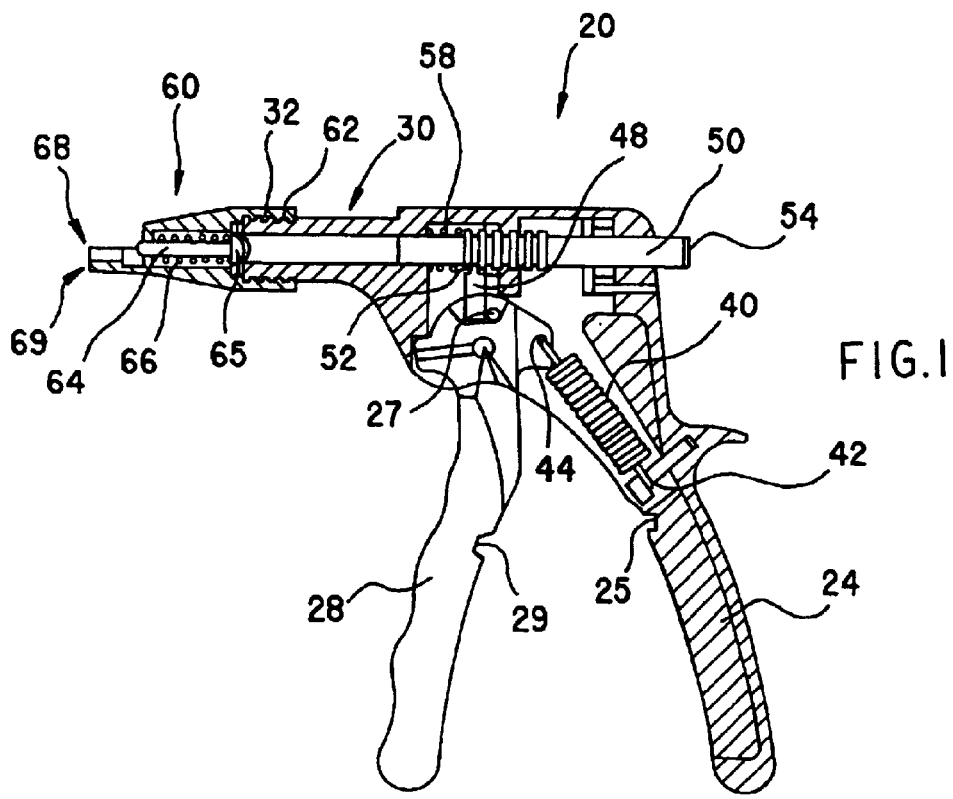
FIG. 1 is a cross-sectional side view of a viscous material dispenser with a small capsule tip assembly attached thereto and with a plunger in a non-extended position, all in accordance with embodiments of this invention.
Figure 2:
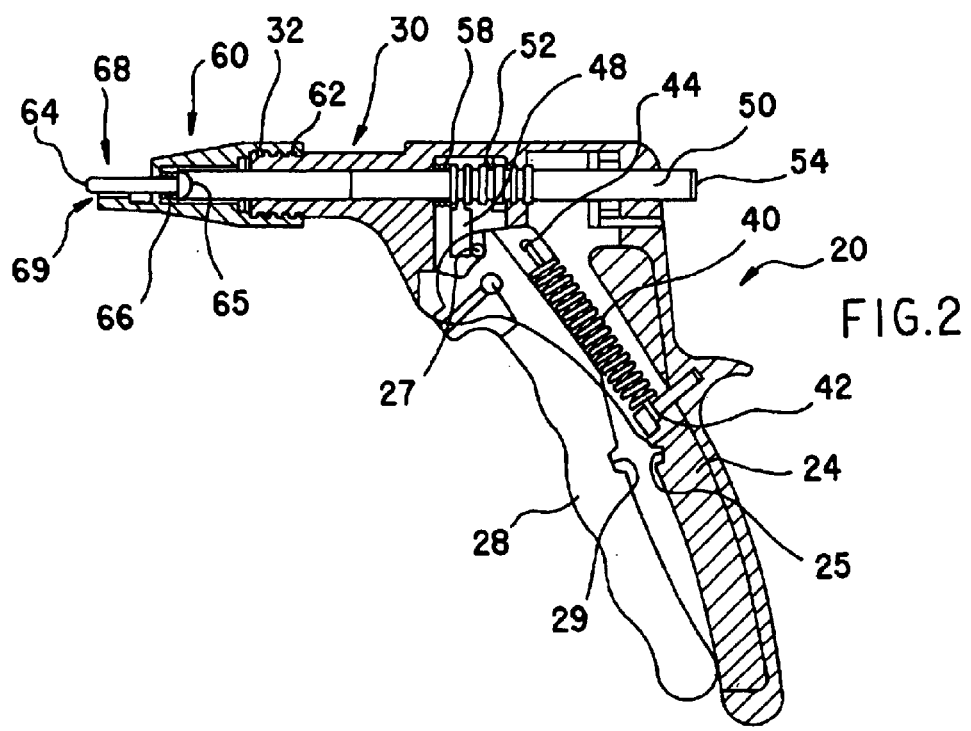
FIG. 2 is a cross-sectional side view of a viscous material dispenser with a small capsule tip assembly attached and with a plunger in a fully-extended position, all in accordance with embodiments of this invention.

Referring now to FIGS. 1–2, a multiple use viscous material dispenser 20 is shown. The dispenser 20 includes a pair of cooperating complementary handles, rear handle 24 and trigger handle 28.

A barrel 30 extends forward toward the dispensing end of the dispenser.

In embodiments of this invention, the external circumference at the dispensing end of the barrel 30 is threaded with, for example, threads 32. The threads 32 can be located at the extreme edge of the barrel 30 or they can be offset from the edge of the barrel 30.

A biasing device or means 40, such as a spring, is positioned between and attached at a spring attachment point 42 on the rear handle 24 and at a spring attachment point 44 on trigger handle 28. The biasing device 40 provides a bias such that, without any squeezing force between the trigger handle 28 and the rear handle 24, the trigger handle 28 and the rear handle 24 will be in a separated configuration, as illustrated in FIG. 1.

A squeezing force applied between the trigger handle 28 and the rear handle 24, against the biasing force of the biasing device 40, will squeeze the handles 28 and 24 closer together, into the configuration illustrated in FIG. 2.

In embodiments, the cooperating trigger handle 28 and rear handle 24 can include a means for activating a multi-component type viscous material containing cartridge (not shown), such as conventional glass ionomer capsules. For example, trigger handle 28 can include an indentation 29 and rear handle 24 can include a corresponding indentation 25. A cartridge of the type that is required to be squeezed against the sides in order to be activated can then be inserted between the trigger handle 28 and the rear handle 24, with sides of the cartridge being supported at the indentation 29 and the indentation 25 in order to keep the cartridge from slipping out from between the trigger handle 28 and rear handle 24.

A squeezing force applied between the trigger handle 28 and the rear handle 24, against the biasing force of the biasing device 40, to squeeze the handles 28 and 24 closer together, will place pressure on the sides of a cartridge supported at the indentations 25 and 29 causing a frangible barrier or the like in the cartridge to break. The cartridge can then be shaken to further mix the components within such a cartridge and to thereby activated the viscous composition.

U.S. Pat. No. 4,671,661 to Herold and U.S. Pat. No. 3,907,106 to Purrmann et al., both of which are hereby incorporated by reference in their entireties, disclose cartridge containers in which mixing is effected by pressure applied in a direction towards a wall of the container, and which are illustrative of the types of cartridges that can be activated using the means for activating discussed above.

In embodiments of this invention, the dispenser 20 can include a ratchet mechanism to reduce the amount of hand pressure necessary to dispense viscous materials. In addition to less pressure, the ratchet mechanism can help ensure that only the amount of viscous material intended is dispsensed. The ratchet mechanism can also assist in locking a cartridge, capsule or the like in place thereby minimizing the possibility of 'fly-off' during application.

In embodiments of this invention, the ratchet mechanism can include a ratcheting pawl 48 that is in contact with a contact pin or tab 27 or the like on the trigger handle 28 and can be moved forward (toward the dispensing end of the barrel) against the force of the biasing device 40 by squeezing of the trigger handle 28. The ratcheting pawl 48 moves rearward (away from the dispensing end of the barrel) by the resilient return force of the spring 40.

A plunger 50 is mounted within the barrel 30. The plunger is urged in a rearward position (away from the dispensing end of the barrel) by the force of a biasing device or means 58, such as and for example a spring.

In embodiments of this invention, the plunger can have external notches 52 which engage with the ratcheting pawl 48. When the trigger handle 28 is squeezed, the contact tab or pin 27 is moved forward toward the dispensing end of the barrel, and the contact tab or pin 27 pushes the ratcheting pawl 48, which is also engaged with a first notch 52 on plunger 50. As the ratcheting pawl 48 is moved forward through the barrel 30 it pushes the plunger 50 forward through the barrel against the force of the biasing device 58. When the trigger handle 28 is released, the ratcheting pawl 48 moves rearward through the barrel along the outside of the plunger and engages with another notch 52 located behind the first notch 52. The plunger 50 can thus be moved forward through the barrel 30 in a "ratcheting" manner.

The ratcheted plunger can be disengaged and released from its extended position by pushing on a button 54 located over the rear portion of the plunger 50.

In embodiments of this invention, different tips for supporting different types of viscous material containing cartridges, capsules, capsules, and the like, can be included with the dispenser 20. For example, a kit can be manufactured which includes a dispenser 20 and two different types of tips, such as tip 70 illustrated in FIGS. 3–4 and tip 60 illustrated in FIGS. 6–7.

Although only two exemplary tips 60 and 70 are described in detail, this invention contemplates other different size and shape tips that can be constructed to accommodate different size and shape capsules, capsules, cartridges and the like.

Figure 7:
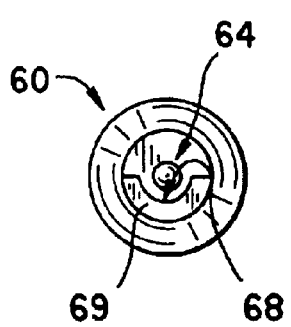
FIG. 7 is a front view of the enlarged small capsule tip assembly of FIG. 6 in accordance with embodiments of this invention.
Figure 6:
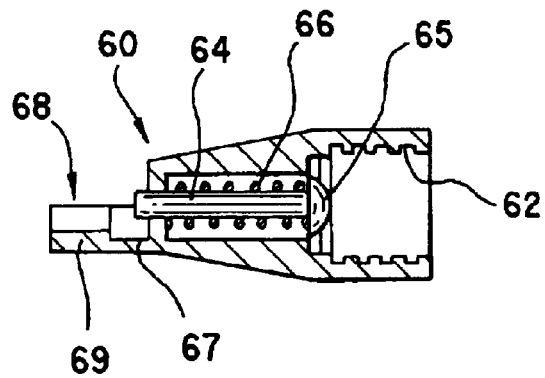
FIG. 6 is an enlarged cross-sectional side view of a small capsule tip assembly in accordance with embodiments of this invention.

For example, one type of tip that can be included with the dispenser 20 is the small capsule tip 60 illustrated in FIGS. 6–7 In embodiments of this invention, the small capsule tip 60 can have an attaching mechanism 62, such as and for example internal threads, which cooperate with an attaching mechanism 32, such as and for example external threads 32, on the end of the barrel 30 of the dispenser 20. Thus, the small capsule tip 60 can be screwed onto and off of the dispenser 20. Of course the small capsule tip 60 and the dispenser 20 can be attached in any other suitable way, such as be means of a bayonet mount, side clips, a breach lock, interrupted threads, clamped flanges, and any and all equivalents thereof, as would be understood by those of skill in the art.

Figure 5:
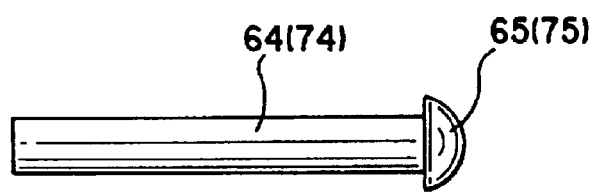
FIG. 5 is an enlarged side view of an actuator that can be used inside a capsule tip in accordance with embodiments of this invention.

The small capsule tip has its own actuator 64 with a back contact piece 65 (shown in more detail in FIG. 5). The back contact piece 65 can be constructed to be contacted by the front end of the plunger 50. A biasing device or means 66, such as and for example a spring, can be used to urge the actuator 64 toward the back (away from the dispensing end 69) of the tip 60.

The tip can have a container slot 68 for retaining a viscous material container such as a cartridge, capsule, or the like (not shown) near the dispensing end 69 of the tip 60. A recess 67 in the container slot 68 can be included to assist in retention of the container by providing a catch for the typical flanged back end included with many conventional dental viscous material containers.

Figure 4:
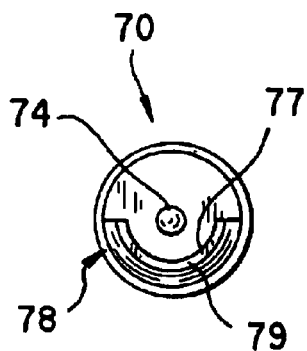
FIG. 4 is a front view of the enlarged large capsule tip assembly of FIG. 3 in accordance with embodiments of this invention.
Figure 3:
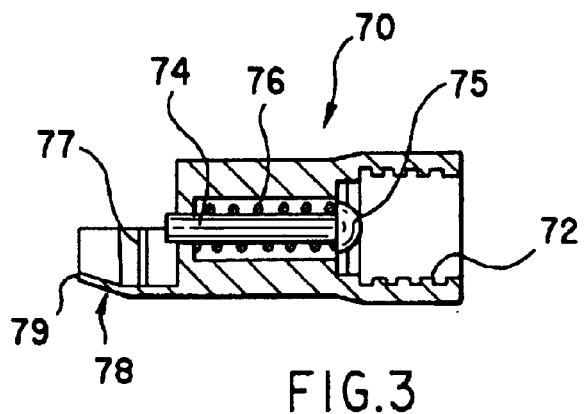
FIG. 3 is an enlarged cross-sectional side view of a large capsule tip assembly in accordance with embodiments of this invention.

Another type of tip that can be used as part of this invention is a large capsule tip 70, as illustrated in FIG. 3–4.

In embodiments of this invention, the large capsule tip 70 can have internal threads 72 which cooperate with the external threads 32 on the end of the barrel 30 of the dispenser 20. Thus, the large capsule tip 70 can be screwed on and off of the dispenser 20. Of course the large capsule tip 70 and the dispenser can be attached in any other suitable way, as noted above with respect to the small capsule tip as would be understood by those of skill in the art.

The large capsule tip 70 has its own actuator 74 with a back contact piece 75. The back contact piece 75 can be constructed to be contacted by the front end of the plunger 50. A biasing device or means 76, such as and for example a spring, can be used to urge the actuator 74 toward the back (away from the dispensing end 79) of the tip 70.

The tip 70 can have a cartridge slot 78 for retaining a cartridge(not shown) near the dispensing end 79 of the tip 70. A raised surface 77 in the cartridge slot 78 can be included to assist in retention of the cartridge by providing a catch for the typical flanged back end included with many conventional dental cartridges.

The system as herein described may be generally applied to a wide variety of viscous materials. However, in particular, viscous material dispenser 20 may be applied to such viscous materials as dental cements and fillers, as well as to glass ionomer cements, adhesives and restorative compositions commonly used in the dental art, as well as to anesthetic compositions.

Subsequent to a tip 60 or 70 being attached to, for example by being screwed onto, the barrel 30, an appropriate conventional viscous material container such as and for examples, a capsule, capsule or cartridge, can be inserted into the slot 68 or 78.

Squeezing the trigger handle 28 will cause the ratcheting pawl 48 to engage with the plunger 50 to ratchet the plunger 50 forward toward the dispensing end of the barrel and to place pressure against the back contact piece of the actuator 65 or 75 causing the actuator 64 or 74 to move forward against the bias of the spring 66 or 76.

The forward motion of the actuator 64 or 74 causes viscous material contained in the conventional viscous material container mounted in the tip 60 or 70 to be expelled in a controlled manner. Typically, the actuator 64 or 74 will press against a piston or similar device on the conventional viscous material container and the piston will be forced through the conventional viscous material container forcing viscous material out of a nozzle or the like in the opposite end of the conventional viscous material container. Some representative examples of conventional viscous material containers, such as cartridges and capsules and the like, that can be utilized in the dispenser of this invention are disclosed in patents listed above in the Background Section and have been incorporated herein by reference.

The pressure on the tip 60 or 70 can then be removed by pushing on a release button 54 attached to the rear of the plunger 50 to release the ratcheted engagement thereof.

Although embodiments of this invention have been described in detail, it will be understood that this invention is not limited to the above-described embodiments, and various modifications in construction may be made without departing from the spirit and scope of this invention and any and all equivalents thereof as defined in the following claims.

What is claimed is:

1. A viscous material dispenser system, comprising:
   a viscous material dispenser having a barrel with a plunger adapted to extend from a dispensing end of the barrel;
   a first tip assembly for retaining a viscous material container, said first tip assembly being attachable to and detachable from the dispensing end of the barrel of the viscous material dispenser and said first tip assembly containing a first actuator, the first actuator being biased such that an end of the first actuator contacts the plunger when the first tip assembly is attached to the barrel and an opposite end of the first actuator adapted for contacting a viscous material container when a viscous material container is retained in the first tip assembly such that movement of the plunger out of the dispensing end of the barrel causes the first actuator to move toward a dispensing end of the first tip assembly;
   wherein the dispenser further comprises a cooperating pair of handles that can be squeezed together, said cooperating pair of handles comprising a means for activating a viscous material cartridge containing a multi-component composition, said means comprising indentations on said pair of handles such that a first indentation on one handle is opposed from a second indention on an opposite handle, said first and second indentations formed to engage sides of the viscous material cartridge.

2. The viscous material system of claim 1, further comprising a second tip assembly for retaining a viscous material containing container, said second tip assembly being different from said first tip assembly, and said second tip assembly being attachable to and detachable from the dispensing end of the barrel and said second tip assembly containing a second actuator, the second actuator being biased such that an end of the second actuator contacts the plunger when the second tip assembly is attached to the barrel and an opposite end of the second actuator adapted for contacting a viscous material container when retained in the second tip assembly such that a movement of the plunger out of the dispensing end of the barrel will cause the second actuator to move toward a dispensing end of the second tip assembly.

3. The viscous material system of claim 2, wherein the barrel of said dispenser has a first set of threads and the first tip assembly has a second set of threads that cooperate with the first set of threads such that the first tip assembly and the barrel of the dispenser can be screwed together, and wherein the second tip assembly has a third set of threads that cooperate with the first set of threads such that the second tip assembly and the barrel of the dispenser can be screwed together.

4. A method of treating a dental patient in need of such treatment, comprising selecting one of said first tip assembly or said second tip assembly according to claim 2, attaching the selected one of said first tip assembly or said second tip assembly to the viscous material dispenser, inserting a viscous dental material container into the selected one of said first tip assembly and said second tip assembly, and utilizing the viscous material dispenser to dispense viscous dental material from the viscous dental material container to the dental area of the dental patient.

5. The viscous material system of claim 1, wherein the barrel of said dispenser has a first set of threads and the first tip assembly has a second set of threads that cooperate with the first set of threads such that the first tip assembly and the barrel of the dispenser can be screwed together.

6. A method of treating a dental patient in need of such treatment, comprising utilizing the viscous material dispenser of claim 1 with said first tip assembly attached and the viscous material container retained therein, to dispense a viscous dental material to the dental area of the dental patient.

7. A viscous material dispenser kit, comprising:
   a container;
   a viscous material dispenser having a barrel with a plunger adapted to extend from a dispensing end of the barrel of the viscous material dispenser, said dispenser being contained in said container;
   a first tip assembly for retaining a viscous material containing cartridge, said first tip assembly being attachable to and detachable from the dispensing end of the barrel of the viscous material dispenser and said first tip assembly containing a first actuator, an end of the first actuator being adapted to contact the plunger when the first tip assembly is attached to the barrel and an opposite end of the first actuator adapted for contacting a viscous material containing cartridge when a viscous material cartridge is retained in the first tip assembly such that a movement of the plunger out of the dispensing end of the barrel will cause the first actuator to move toward a dispensing end of the first tip assembly, said first tip assembly being contained in said container;
   a second tip assembly for retaining a viscous material containing capsule, said second tip assembly being different from said first tip assembly, and said second tip assembly being attachable to and detachable from the dispensing end of the barrel of the viscous material dispenser and said second tip assembly containing a second actuator, an end of the second actuator being adapted to contact the plunger when the second tip assembly is attached to the barrel and an opposite end of the second actuator adapted for contacting a viscous material containing capsule when a viscous material capsule is retained in the second tip assembly such that a movement of the plunger out of the dispensing end of the barrel will cause the second actuator to move toward a dispensing end of the second tip assembly, the second tip assembly being contained in said container;

wherein the dispenser further comprises a cooperating pair of handles that can be squeezed together, said cooperating pair of handles comprising a means for activating a viscous material cartridge containing a multi-component composition, said means comprising indentations on said pair of handles such that a first indentation on one handle is opposed from a second indention on an opposite handle, said first and second indentations formed to engage sides of the viscous material cartridge.

8. The viscous material kit of claim 7, wherein the barrel of said dispenser has a first set of threads and the first tip assembly has a second set of threads that cooperate with the first set of threads such that the first tip assembly and the barrel of the dispenser can be screwed together, and wherein the second tip assembly has a third set of threads that cooperate with the first set of threads such that the second tip assembly and the barrel of the dispenser can be screwed together.

9. A viscous material dispenser, comprising:

means for moving a plunger through a barrel of a viscous material dispenser such that the plunger extends from a dispensing end of the barrel;

a first means for retaining a viscous material containing capsule, said first means being attachable to and detachable from the dispensing end of the barrel and said first means containing a first actuating means being contacted by the plunger when the first means is attached to the barrel and an opposite end of the first actuating means adapted for contacting a viscous material capsule when a viscous material capsule is retained in the first means such that a movement of the plunger out of the dispensing end of the barrel will cause the first actuating means to move toward a dispensing end of the first tip assembly;

wherein the dispenser further comprises a cooperating pair of handles that can be squeezed together, said cooperating pair of handles comprising a means for activating a viscous material cartridge containing a multi-component composition, said means comprising indentations on said pair of handles such that a first indentation on one handle is opposed from a second indention on an opposite handle, said first and second indentations formed to engage sides of the viscous material cartridge.

10. The viscous material dispenser of claim 9, further comprising a second means for retaining a viscous material containing capsule, said second means being different from said first means, and said second means being attachable to and detachable from the dispensing end of the barrel of the viscous material dispenser and said second means containing a second actuating means, an end of said second actuating means being adapted to be contacted by the plunger when the second means is attached to the barrel and an opposite end of the second actuating means adapted for contacting a viscous material capsule when a viscous material capsule is retained in the second means such that a movement of the plunger out of the dispensing end of the barrel will cause the second actuating means to move toward a dispensing end of the second means.

11. The viscous material dispenser of claim 10, further comprising means for attaching the barrel in coaxial alignment with either of the first means and the second means.

12. The viscous material dispenser of claim 9, further comprising means for attaching the barrel and the first means in coaxial alignment.

13. The viscous material dispenser of claim 12, wherein the means for attaching comprises threads on the barrel of the dispenser and threads on the first means such that the dispenser and the first means can be screwed together.

14. The viscous material dispenser of claim 13 wherein the means for attaching comprises threads on the barrel of the dispenser that cooperate with either of threads on the first means and threads on the second means such that the dispenser can be screwed together with either of the first means and the second means.

15. A viscous material dispenser system, comprising:

a viscous material dispenser having a barrel with a plunger adapted to extend from a dispensing end of the barrel;

the dispenser further having a cooperating pair of handles that can be squeezed together, said cooperating pair of handles comprising a means for activating a viscous material cartridge containing a multi-component composition, said means comprising indentations on said pair of handles such that a first indentation on one handle is opposed from a second indention on an opposite handle, said first and second indentations formed to engage sides of the viscous material cartridge.

* * * * *